United States Patent [19]

North et al.

[11] Patent Number: 5,344,544
[45] Date of Patent: Sep. 6, 1994

[54] DIAGNOSTIC ELECTRODE FOR EVALUATING CIRCUITRY OF AN ANALYZER

[75] Inventors: John R. North, Salisbury, United Kingdom; Robert L. Kay, Thousand Oaks; Jonathan Ivy, Ventura, both of Calif.

[73] Assignee: Porton Diagnostics, Inc., Westlake Village, Calif.

[21] Appl. No.: 909,322

[22] Filed: Jul. 6, 1992

[51] Int. Cl.$^5$ ............................................. G01W 27/26
[52] U.S. Cl. .................... 204/401; 204/406; 204/407
[58] Field of Search ................... 204/401, 406, 407

[56] References Cited

U.S. PATENT DOCUMENTS

| | | | |
|---|---|---|---|
| 4,622,844 | 11/1986 | Bienkowski | 204/401 |
| 4,702,816 | 10/1987 | Hashimoto et al. | 204/406 |
| 4,999,582 | 3/1991 | Parks et al. | 204/406 |

Primary Examiner—John Niebling
Assistant Examiner—Bruce F. Bell
Attorney, Agent, or Firm—Kenyon & Kenyon

[57] ABSTRACT

A diagnostic electrode actively generates test signals to be supplied to analyzer circuitry. The electrode emulates a disposable sensor associated with the analyzer during a normal mode of normal operation. The diagnostic device generates predetermined signals for an output interface of the device using a power supply disposed within the device. The diagnostic module can be designed to produce voltage signals, current signals, or light signals to be received by the analyzer, depending on the type of analyzer to which the diagnostic electrode is to be associated.

27 Claims, 4 Drawing Sheets

DIAGNOSTIC ELECTRODE FOR EVALUATING CIRCUITRY OF AN ANALYZER

BACKGROUND OF THE INVENTION

1. Field of the Invention

The present invention relates to a diagnostic electrode to be used to supply reference signals to an analyzer circuit. More specifically, the diagnostic electrode includes an active signal generating circuit which creates reference signals to be received and analyzed by the analyzer circuitry.

2. Related Art

It is known to provide an analyzer that includes circuitry for receiving input data related to a test sample and determining characteristics of that test sample based on that data. It is also known to provide a sample holding device to be in contact with the analyzer and thus transmit input information to the analyzer circuitry.

An example of such an analyzer circuitry is described in U.S. patent application Ser. No. 07/750,534 filed Aug. 27, 1991. An example of a known analyzer utilizing such analyzer-circuitry is the STAT-K ANALYZER, (a trademarked product of Porton Diagnostics Inc.), which is described in U.S. patent application Ser. No. 07/763,696 filed Sep. 23, 1991. The disclosures of these two patent applications are hereby incorporated by reference. An example of a sample holding device is disclosed in U.S. patent application Ser. No. 07/401,786, filed Sep. 1, 1989, directed to a disposable sensor.

The STAT-K ANALYZER is constructed so that a disposable sensor can be inserted into a receiving portion of the analyzer. The disposable sensor is designed to receive a sample of the material to be analyzed, and the interface between the sensor and the analyzer conveys information about the sample from the sensor to the analyzer circuitry. That circuitry then interprets that information to determine characteristics of the sample. The analyzer and associated sensor electrode are generally employed for medical purposes and analyze a material, such as blood, by studying the ion content of the material.

The disposable sensor is precalibrated and thus has an initial known ion concentration. When the sample is placed on a receiving region of the disposable sensor, the ions in the sample interact and/or pass through an ion selective membrane of the sensor so as to create an ion imbalance representative of a change in ion concentration. The analyzer circuit detects the ion imbalance and then determines the ion concentration in the sample disposed on the sensor.

In a preferred embodiment the disposable sensor is used only once, i.e., the sensor is used to analyze only one sample and then the user of the analyzer circuit discards the sensor.

The accuracy of any analytical device, especially those used for medical purposes, is most important to the user and must be checked at regular intervals. It is common to provide a daily check of the accuracy of an analytical device as part of a regular quality control routine. Where, as here, the analytical system includes an analyzer and a removable or disposable sensor, inaccuracies in performance can arise from at least three different circumstances. First, inaccuracy can be the result of a failure of the sensor. Inaccuracy can also be the result of a failure in the analyzer. Finally, inaccuracy can be the result of a failure in the interface between the sensor and the analyzer. Typically, when inaccurate results are detected, it is necessary to attempt to isolate the failure in one of these three areas. One possible method for checking the accuracy of the system is to separate the sensor and the analyzer which together have produced the faulty result and separately test the sensor with a different analyzer while testing the analyzer with a different sensor.

There are shortcomings with this evaluation procedure, especially where one of the components, e.g., the sensor, can only be used once. In a two component system it is conceivable that a second sensor will not be more accurate than the sensor involved in the failure. In fact, since single-use sensors may be produced in batches, it is possible that each sensor in the same batch as the sensor involved in the failure will have the same or similar defect. Where batch sizes are large, it may happen that many, if not all, of the sensors available to a given user are from the same batch and thus, all of the sensors in the possession of the user may have the same defect.

Thus, where an analyzer employs a single-use detector module and results have been found to be inaccurate, a conventional problem arises in making an early decision whether to obtain a new batch of the sensors and/or to call expert service for remedial work on the analyzer.

It is known from U.S. Pat. No. 4,882,544 to Uekusa to supply an inspection device for an analyzer for ionic activity. Uekusa provides a passive resistive device as an inspection device. The inspection device has outer dimensions approximately equal to the outer dimensions of a sample measuring device. However, before the analyzer can detect any signals from the inspection device so that the operational capabilities of the analyzer circuitry can be evaluated, the possibly faulty analyzer circuitry itself must supply signals to the passive inspection device. Thus, the reference signal used to test the analyzer circuitry is dependent on the analyzer. This can result in a skewed analysis of the functional capabilities of the analyzer.

SUMMARY OF THE INVENTION

The present invention provides the flexibility of periodically testing circuitry in an analyzer by providing a diagnostic module that is insertable and removable from an electrode-receiving area of an analyzer. The module is designed as a diagnostic electrode that may be substituted for a disposable sensor. The diagnostic electrode may include an output interface that couples the electrode to an input of the analyzer circuitry in a manner similar to the way the disposable sensor is coupled to the input interface of the analyzer. The module may also contain a power supply and a reference signal generator that is responsive to the power supply and which actively generates a reference signal and applies that signal to the output interface of the module. As a consequence, the module is designed to produce a reference output signal to which the analyzer circuitry should respond in a predictable fashion if that circuitry is operating properly. If the circuitry produces an unexpected result based on the input received from the module, then it is likely that there is a failure in the circuitry.

The module simulates a single use sensor with regard to its mechanical and electronic or optical interfaces with the analyzer. The module can provide a predetermined standardized voltage or current output, or it can supply a standardized light output that falls within the normal range of output of a typical sensor. Thus, the module constitutes a device that permits a user to determine whether the analyzer to which it is connected is performing accurately, separate from the performance of a single use sensor.

DETAILED DESCRIPTION

Figure 1:
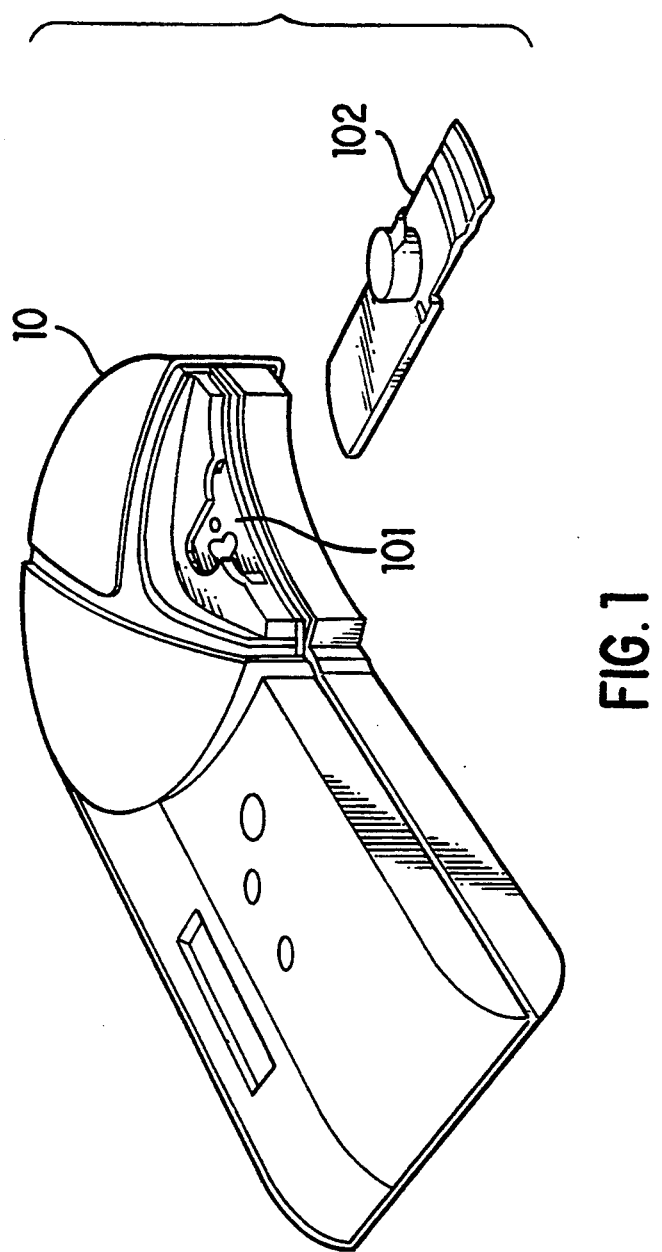
FIG. 1 illustrates a perspective view of a known analyzer device with a disposable sensor with which the device operates.

FIG. 1 illustrates a perspective view of an analyzer device 10 and disposable sensor 102 disclosed in U.S. patent application Ser. No. 07/763,696. Area 101 is a sensor receiving area. Typically, the single use or "disposable" sensor 102 is inserted into area 101. A sample is then disposed on the sensor which then, through an output interface, provides input signals to an analyzer circuitry within the body of the analyzer. In the analyzer of the related application, the circuitry detects ion activity in a sample of blood so as to provide information about the characteristics of the blood sample. This particular analyzer circuitry has an input that consists of a potential that exists across three output electrodes of the disposable sensor as a consequence of the placement of the sample on a sample receiving region of the sensor. The analyzer circuitry processes the input information and determines the ion content of the sample placed on the disposable sensor.

Figure 2:
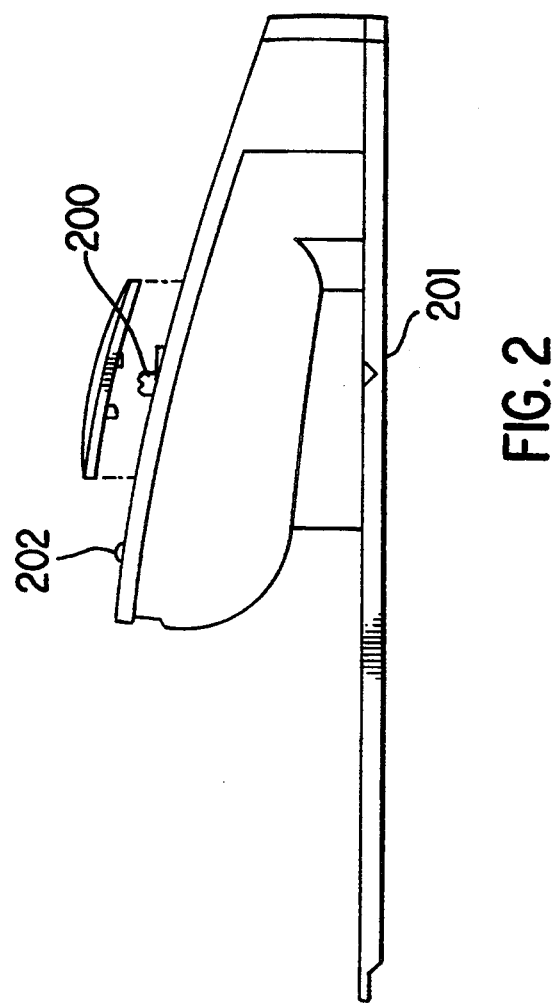
FIG. 2 illustrates an elevation view of a diagnostic electrode as a testing module according to an embodiment of the present invention.

FIG. 2 illustrates an elevation view of diagnostic electrode as the testing module according to an embodiment of the present invention. The diagnostic electrode includes an output interface 201 capable of interacting with an input interface of the analyzer of FIG. 1. The diagnostic electrode is insertable into the disposable sensor receiving area 101 of the analyzer. The output interface of the diagnostic electrode is similar in configuration to the output interface of the disposable sensors 102. The diagnostic electrode has a switch 200 which can be accessed by user so as to control the turning on and turning off of the diagnostic electrode. The electrode also has a light emitting portion 202 to provide a visual indication about the status of the electrode's power supply.

Since the analyzer circuitry is responsive to potential differences produced by the sensor devices and supplied to the input interface of the analyzer circuit, the diagnostic electrode of this embodiment is designed to provide preselected potentials across the output electrodes of the diagnostic device. The analyzer circuit is then expected to respond in a predetermined fashion to these predetermined potentials.

Figure 3:
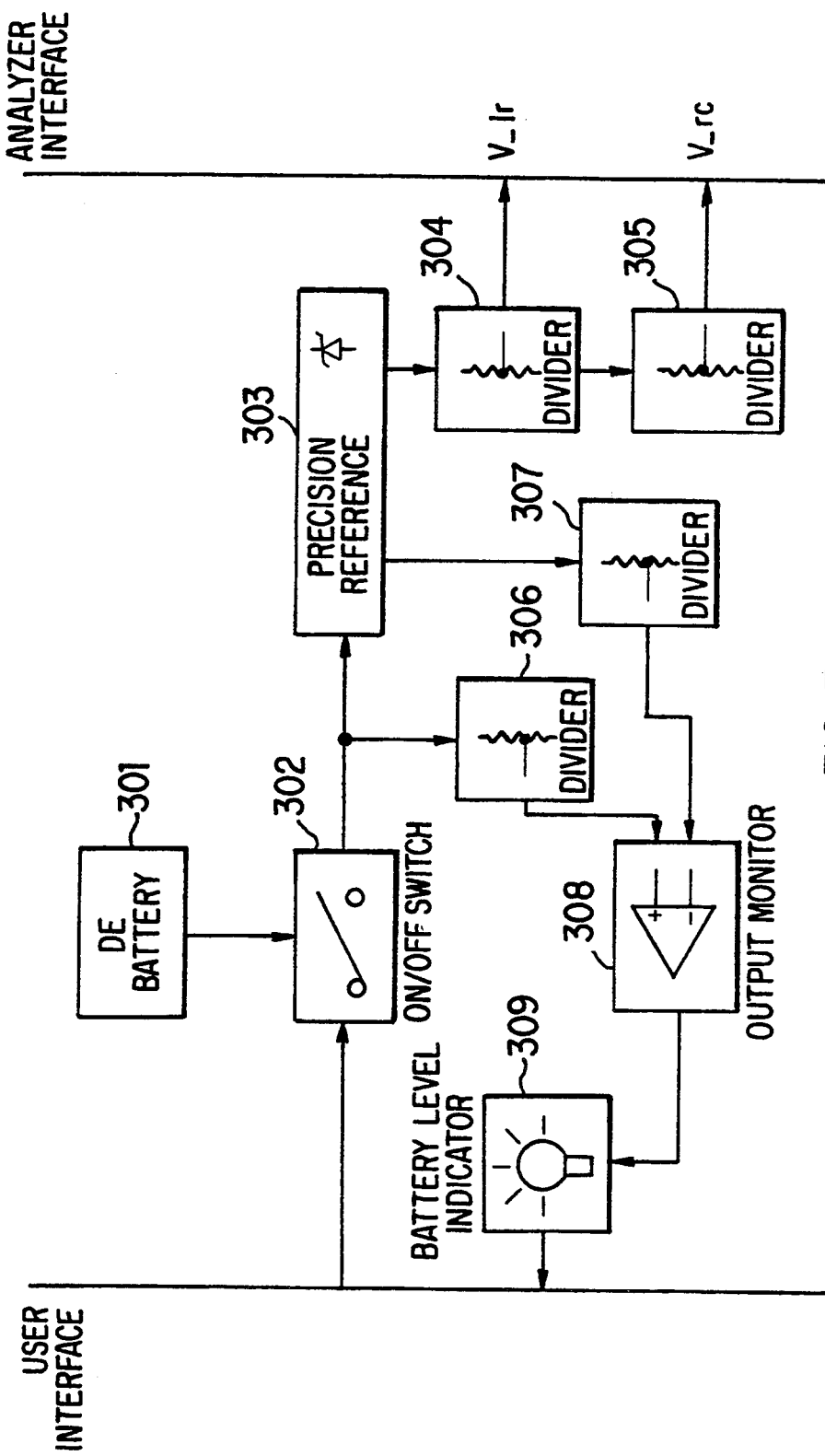
FIG. 3 illustrates an embodiment of a signal generator circuit to be employed within the diagnostic electrode of FIG. 2.

FIG. 3 illustrates a block diagram representation of the circuitry which can be used in a diagnostic electrode for producing the reference potentials at the electrodes of the diagnostic device.

The embodiment of the diagnostic electrode illustrated in FIG. 3 presumes an interface with analyzer circuitry similar to that disclosed in U.S. patent application Ser. No. 07/750,534. That analyzer circuitry has 3 input electrodes, a left electrode, a right electrode and a center electrode. FIG. 3 illustrates that the diagnostic electrode has an analyzer interface and a user interface. The diagnostic electrode also includes a power supply, battery 301. An ON/OFF switch 302, which can be a simple slide switch accessible by the user, controls the connection of the power supply to the remainder of the diagnostic electrode circuitry. When the switch is in the ON position, power is supplied to a precision reference generator 303. This reference generator receives the power supplied by the battery through the ON/OFF switch and generates a precise potential level. That potential level is subsequently divided by voltage dividers 304 and 305. The potentials produced across these two voltage dividers are supplied as outputs of the diagnostic electrode. The potential produced across voltage divider 304 is applied as a voltage to the left and right electrodes of the analyzer circuitry. The potential across the voltage divider 305 is provided as an input voltage for the right and center electrodes of the analyzer circuitry. The power supply voltage applied to the precision reference generator is subjected to voltage division by voltage divider 306 and the output of the precision reference generator 303 is further subjected to voltage division by voltage divider 307. The outputs of these two voltage dividers 306 and 307 are inputs to an output monitor amplifier 308. That monitor amplifier determines whether the voltage difference between the outputs of dividers 306 and 307 exceeds a predetermined threshold. When it does, the monitor amplifier 308 provides an output signal that powers a small light source, such as a light emitting diode 309 which indicates to the user that the battery level in the diagnostic electrode is sufficient. When the difference between the outputs of dividers 306 and 307 is below the predetermined threshold, the output monitor does not produce a signal sufficient to light the LED. The user is thus advised that the battery level of the diagnostic electrode has fallen below that necessary for the device to operate effectively.

The voltage supplied by the voltage dividers 304 and 305 can be selected to test any desired response of the associated analyzer circuitry. For example, the analyzer may be typically used to test a sample to determine if an ion content is within an acceptable range and will provide a warning indication if the ion concentration is detected to be outside of the range. The outputs for the voltage dividers can be selected to provide voltages that are within a range corresponding to an acceptable ion content or can be selected to be outside of the desired range so as to test both the operation of the analyzer circuitry and the analyzer warning mechanism. In addition, the output voltage values can be selected to fall within a narrow range so as to detect the detection precision available with the analyzer circuitry.

Figure 4:
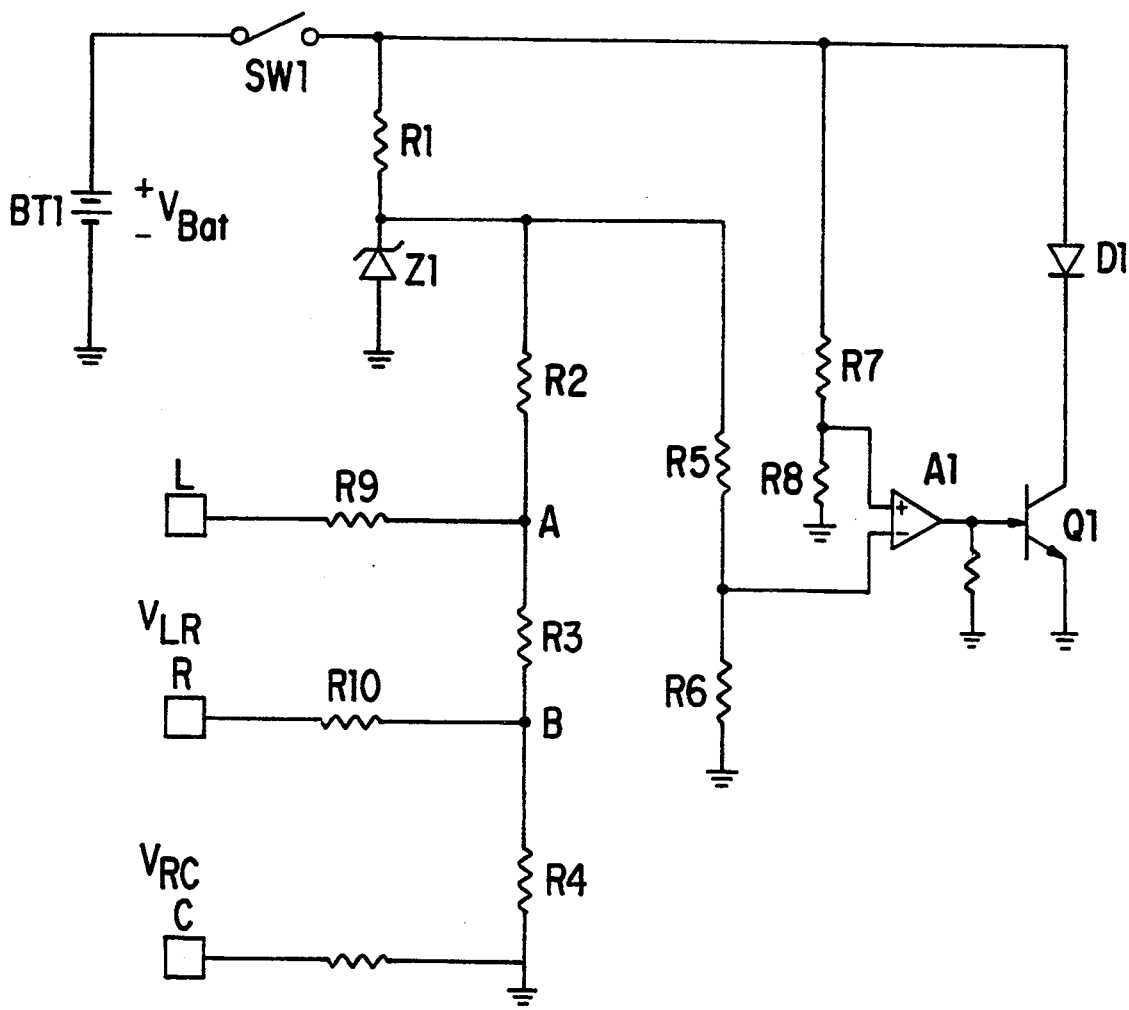
FIG. 4 illustrates a more detailed circuit diagram of the signal generator of FIG. 3.

FIG. 4 illustrates a circuit diagram for implementing the embodiment disclosed in FIG. 3. A battery BT1 provides a voltage $V_{Bat}$. Resistance R1 and a zener diode Z1 are connected in series with one another, but in parallel with the battery when switch SW1 is in the ON or closed position. A reference voltage is developed across the zener diode Z1. A voltage divider, consisting of resistances R2, R3 and R4, is connected in parallel with the zener diode Z1 and thus divides the reference voltage developed across that diode into voltages at node A and node B. The circuit provides an output interface to the analyzer circuitry to the connectors (or electrode contacts) L, R, and C. Each connector is respectively connected to one of the analyzer electrodes, the left electrode, right electrode and center electrode. Node A is connected to connector L via resistor R9 and node B is connected to connector R via resistor R10. The result is the development of the potential differences $V_{LR}$ and $V_{RC}$ which are applied to the left and right electrode, and the right and center electrodes of the analyzer circuitry respectively when the diagnostic electrode is coupled to the analyzer.

Furthermore, the resistor R9 simulates the high resistance of a membrane normally associated with a disposable electrode which the diagnostic electrode simulates. It is used to detect excessive bias current failure in the analyzer.

A second voltage divider, including series resistances R5 and R6, is also connected in parallel across the zener diode Z1. The second divider develops a first input to the negative input of amplifier A1. A third voltage divider, constituted by series resistances R7 and R8, is connected in parallel with the battery and develops the positive input for amplifier A1. When the difference between the input from the third voltage divider and the input from the second voltage divider is sufficiently high, transistor Q1 is turned on. As a consequence, a current path through a light emitting diode D1 is created, and current originating from the battery source across which D1 and transistor Q1 are connected in parallel causes the D1 to be illuminated. When the difference between the output of the third voltage divider and the second voltage divider is smaller than the threshold value, then Q1 remains OFF and no current flows through the D1 and thus it does not light. This indicates to the user that the diagnostic electrode does not have sufficient power to operate effectively.

The above embodiment presumes the application of specified voltages or potentials to the analyzer circuitry. This particular design is useful in connection with a known analyzing device which receives and studies potentials generated by ion selective electrodes. The number of output potentials can be designed to match the number of inputs which the analyzer expects to receive from a disposable sensor.

Other designs for the diagnostic electrode, which take into account the operation of other types of analyzers are possible.

For example, it is conceivable that an analyzer may be adapted to receive current signals from disposable sensors. Such disposable sensors may utilize oxidoreductase enzymes that are linked by electron transfer mechanisms to an electro-conductive material. In such an instance, the diagnostic electrode would then mimic the disposable sensor by producing currents to be received by the input electrodes of the analyzer circuitry rather than voltage potentials. However, like the potentiometric diagnostic electrode described with respect to FIGS. 3 and 4, an amperometric device would require an active signal source, typically a battery-powered controlled current device, mounted in the diagnostic electrode.

Another example of an analyzer is one that measures the intensity or wavelength of light. In these circumstances, a disposable sensor or detector may produce a varying light signal as an output, with the signal varying either in wavelength or intensity, to indicate the characteristics of a sample that is under test. In this circumstance, a diagnostic electrode would emulate the disposable detection module by producing a light signal to be supplied to the input interface of the analyzer via an output interface of the diagnostic electrode. The testing module would be designed according to whether the analyzer detected wave length changes or intensity changes. This embodiment of a diagnostic electrode would also contain a battery-powered light source that would supply either a designated light intensity to the analyzer or specific light wave length to the analyzer. Such a diagnostic electrode could simulate detector modules which generate light output signals through surface plasmon resonance, analyte-modulated fluorescence, or chemiluminescence.

In summation, the present invention provides a testing module that actively generates test signals to be supplied to an analyzer so as to evaluate the operational capabilities of the analyzer. The testing module is adapted to produce output signals at an output interface and those signals emulate signals produced by a disposable sensor which would interface with the analyzer under normal operating conditions. The diagnostic electrode includes a power source for generating the simulated output signals. As a consequence, the diagnostic electrode provides a capability of testing the analyzer to assure its operational integrity as part of a regular routine to guarantee super operation of the analyzer before testing samples with disposable sensors.

What is claimed is:

1. An apparatus for testing circuit operation of an analyzer comprising:
   a power source;
   a reference signal generator, coupled to said power source and generating a reference signal based on said power source; and
   an output interface adapted to supply said reference signal to the analyzer.

2. The apparatus of claim 1 wherein said output interface simulates an output of a sampling device and said reference signal emulates a signal from the sampling device.

3. The apparatus of claim 1 wherein said reference signal generator comprises a first voltage source producing a first voltage difference at said output interface and a second voltage source producing a second voltage difference at said output interface.

4. The apparatus of claim 2 wherein said reference signal generator comprises a first voltage source producing a first voltage difference at said output interface and a second voltage source producing a second voltage different at said output interface.

5. The apparatus of claim 1 wherein said reference signal is a reference current signal to be supplied to the analyzer.

6. The apparatus of claim 2 wherein said reference signal is a reference current signal to be supplied to the analyzer.

7. The apparatus of claim 1 wherein said reference signal includes a light signal of a set intensity and wavelength.

8. The apparatus of claim 1 wherein said output interface comprises a plurality of electrode contacts and said reference signal generator comprises:
   a first reference circuit developing a first reference voltage differential; and
   a second reference circuit dividing said first reference voltage differential into a plurality of output voltage differentials applied to said plurality of electrode contacts.

9. The apparatus of claim 2 wherein said output interface comprises a plurality of electrode contacts and said reference signal generator comprises:
   a first reference circuit developing a first reference voltage differential; and
   a second reference circuit dividing said first reference voltage differential into a plurality of output voltage differentials applied to said plurality of electrode contacts.

10. A diagnostic electrode for supplying reference signals to an analyzing device that has an input interface adapted to receive a removable sensor, the electrode comprising:
   a body shaped to mimic the outer contours of the removable sensor;
   an active signal source;
   an output interface coupled to said active signal source adapted to connect the electrode to the input interface of the analyzer in the same manner that the removable sensor is coupled to the input interface.

11. The diagnostic electrode of claim 10 wherein said active signal source comprises a first power source and a reference signal generator coupled to said first power source and said output interface.

12. The apparatus of claim 11 wherein said reference signal generator comprises a first voltage source producing a first voltage difference at said output interface and a second voltage source producing a second voltage difference at said output interface.

13. The apparatus of claim 10 wherein said output interface comprises a plurality of electrode contacts and said active signal source comprises:
   a first reference circuit developing a first reference voltage differential; and
   a second reference circuit dividing said first reference voltage differential into a plurality of output voltage differentials applied to said plurality of electrode contacts.

14. The apparatus of claim 11 wherein said output interface comprises a plurality of electrode contacts and said reference signal generator comprises:
   a first reference circuit developing a first reference voltage differential; and
   a second reference circuit dividing said first reference voltage differential into a plurality of output voltage differentials applied to said plurality of electrode contacts.

15. The apparatus of claim 10 wherein said reference signal is a reference current signal to be supplied to the analyzer.

16. The apparatus of claim 11 wherein said reference signal is a reference current signal to be supplied to the analyzer.

17. The apparatus of claim 10 wherein said reference signal includes a light signal of a set intensity and wavelength.

18. The apparatus of claim 11 wherein said reference signal includes a light signal of a set intensity and wavelength.

19. A testing module, insertable into a sensor receiving area of an analyzer and supplying a reference signal to analyzing circuitry in the analyzer, the module comprising:
   an output interface coupled to an input interface of the analyzer when the module is disposed in the sensor receiving area;
   a reference signal generator, coupled to said output interface and supplying a reference signal to said output interface; and
   means for energizing said reference signal generator, said means for energizing comprising,
      a power supply, and
      means for controlling a coupling of said power supply and said reference signal generator.

20. The apparatus of claim 19 wherein said output interface simulates an output of a sampling device and said reference signal emulates a signal from the sampling device.

21. The apparatus of claim 19 wherein said reference signal generator comprises a first voltage source producing a first voltage difference at said output interface and a second voltage source producing a second voltage difference at said output interface.

22. The apparatus of claim 19 wherein said reference signal is a reference current signal to be supplied to the analyzer.

23. The apparatus of claim 19 wherein said reference signal includes a light signal of a set intensity and wavelength.

24. The apparatus of claim 19 wherein said output interface comprises a plurality of electrode contacts and said reference signal generator comprises:
   a first reference circuit developing a first reference voltage differential; and
   a second reference circuit dividing said first reference voltage differential into a plurality of output voltage differentials applied to said plurality of electrode contacts.

25. The apparatus of claim 1 wherein said output interface includes a plurality of nodes at least one of which includes a means for detecting an excessive bias current failure in the analyzer.

26. The apparatus of claim 25 wherein said means for detecting comprises a high impedance resistor.

27. The apparatus of claim 1 wherein said output interface includes a plurality of nodes at least one of which includes a means for simulating the resistance of a disposable electrode membrane.

* * * * *